(12) United States Patent
Triebes et al.

(10) Patent No.: US 7,124,489 B2
(45) Date of Patent: Oct. 24, 2006

(54) PROCESS FOR PRODUCING A CATHETER

(75) Inventors: Thomas Gregory Triebes, Alpharetta, GA (US); Michael Allen Kenowski, Pocatello, ID (US); Donald J. McMichael, South Jordan, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 81 days.

(21) Appl. No.: 10/306,992

(22) Filed: Nov. 30, 2002

(65) Prior Publication Data

US 2004/0103518 A1    Jun. 3, 2004

(51) Int. Cl.
*A61M 25/00* (2006.01)

(52) U.S. Cl. .................. 29/428; 29/527.1; 604/915; 604/921; 264/239; 264/259

(58) Field of Classification Search .............. 29/428, 29/527.1, 271.1; 604/915, 921; 264/239, 264/259
See application file for complete search history.

(56) References Cited

U.S. PATENT DOCUMENTS

| | | | |
|---|---|---|---|
| 1,598,293 A | | 8/1926 | Kinney |
| 3,050,066 A | | 8/1962 | Koehn |
| 3,544,668 A | | 12/1970 | Dereniuk |
| 3,865,666 A | | 2/1975 | Shoney |
| 3,915,171 A | | 10/1975 | Shermeta |
| 3,959,429 A | | 5/1976 | Benning |
| 4,157,094 A | * | 6/1979 | Patel .................. 604/98.01 |
| 4,210,478 A | | 7/1980 | Shoney |
| 4,213,461 A | | 7/1980 | Pevsner |
| 4,227,293 A | | 10/1980 | Taylor |
| 4,284,459 A | * | 8/1981 | Patel et al. .................. 156/245 |
| 4,315,513 A | | 2/1982 | Nawash et al. |
| 4,393,873 A | | 7/1983 | Nawash et al. |
| 4,447,228 A | | 5/1984 | Patel |
| 4,531,943 A | | 7/1985 | Van Tassel et al. |
| 4,634,435 A | | 1/1987 | Ingraham |
| 4,639,252 A | | 1/1987 | Kelly et al. |
| 4,661,095 A | * | 4/1987 | Taller et al. .................. 604/103 |
| 4,666,433 A | | 5/1987 | Parks |
| 4,685,901 A | | 8/1987 | Parks |
| 4,737,219 A | | 4/1988 | Taller et al. |
| 4,798,592 A | | 1/1989 | Parks |
| 4,850,953 A | | 7/1989 | Haber et al. |

(Continued)

FOREIGN PATENT DOCUMENTS

CA        2019886        1/1991

(Continued)

OTHER PUBLICATIONS

Patent Abstracts of Japan, Publication No. 03277374 A, Dec. 9, 1991.

(Continued)

*Primary Examiner*—Jermie E. Cozart
(74) *Attorney, Agent, or Firm*—Scott B. Garrison; William W. Letson

(57) ABSTRACT

A process for producing a catheter having a head, a shaft, a distal end, and a tip member wherein the tip member is secured onto the distal end of the catheter during production of the tip member. Another embodiment of the present invention is directed to a process for producing a catheter. The process including providing a catheter with a proximal end, a shaft, an interior, an exterior, and a distal end; and producing a balloon member having a proximal end and a distal end; wherein the distal end of the balloon member is attached to the distal end of the catheter during production of the balloon member.

6 Claims, 5 Drawing Sheets

U.S. PATENT DOCUMENTS

| | | | |
|---|---|---|---|
| 4,874,373 A | 10/1989 | Luther et al. | |
| 4,886,059 A | 12/1989 | Weber | |
| 4,927,412 A | 5/1990 | Menasche | |
| 4,950,239 A * | 8/1990 | Gahara et al. | 604/96.01 |
| 4,976,710 A | 12/1990 | Mackin | |
| 5,009,639 A | 4/1991 | Keymling | |
| 5,042,976 A * | 8/1991 | Ishitsu et al. | 604/96.01 |
| 5,074,845 A | 12/1991 | Miraki et al. | |
| 5,076,268 A | 12/1991 | Weber | |
| 5,080,650 A | 1/1992 | Hirsch et al. | |
| 5,087,394 A | 2/1992 | Keith | |
| 5,125,897 A | 6/1992 | Quinn et al. | |
| 5,137,671 A | 8/1992 | Conway et al. | |
| 5,156,612 A | 10/1992 | Pinchuk et al. | |
| 5,195,969 A | 3/1993 | Wang et al. | |
| 5,250,040 A | 10/1993 | Parks et al. | |
| 5,267,969 A | 12/1993 | Hirsch et al. | |
| 5,295,969 A | 3/1994 | Fischell et al. | |
| 5,308,325 A | 5/1994 | Quinn et al. | |
| 5,324,260 A | 6/1994 | O'Neill et al. | |
| 5,370,618 A | 12/1994 | Leonhardt | |
| 5,370,899 A | 12/1994 | Conway et al. | |
| 5,391,159 A | 2/1995 | Hirsch et al. | |
| 5,411,477 A * | 5/1995 | Saab | 604/103.13 |
| 5,423,760 A | 6/1995 | Yoon | |
| 5,439,444 A | 8/1995 | Andersen et al. | |
| 5,458,583 A | 10/1995 | McNeely et al. | |
| 5,514,153 A | 5/1996 | Bonutti | |
| 5,522,961 A | 6/1996 | Leonhardt | |
| 5,527,280 A | 6/1996 | Goelz | |
| 5,593,718 A | 1/1997 | Conway et al. | |
| 5,707,357 A | 1/1998 | Mikhail et al. | |
| 5,709,691 A | 1/1998 | Morejon | |
| 5,718,712 A | 2/1998 | Bonnal et al. | |
| 5,718,861 A | 2/1998 | Andrews et al. | |
| 5,762,996 A | 6/1998 | Lucas et al. | |
| 5,792,118 A | 8/1998 | Kurth et al. | |
| 5,807,520 A | 9/1998 | Wang et al. | |
| 5,836,924 A | 11/1998 | Kelliher et al. | |
| 5,860,952 A | 1/1999 | Quinn | |
| 5,860,960 A | 1/1999 | Quinn | |
| 5,865,721 A | 2/1999 | Andrews et al. | |
| 5,865,816 A | 2/1999 | Quinn | |
| 5,879,499 A | 3/1999 | Corvi | |
| 5,891,113 A | 4/1999 | Quinn | |
| 5,910,128 A | 6/1999 | Quinn | |
| 5,938,585 A | 8/1999 | Donofrio | |
| 5,971,954 A | 10/1999 | Conway et al. | |
| 5,997,503 A | 12/1999 | Willis et al. | |
| 5,997,546 A | 12/1999 | Foster et al. | |
| 6,013,054 A | 1/2000 | Jiun Yan | |
| 6,077,243 A | 6/2000 | Quinn | |
| 6,129,713 A | 10/2000 | Mangosong et al. | |
| 6,136,258 A | 10/2000 | Wang et al. | |
| 6,168,748 B1 | 1/2001 | Wang et al. | |
| 6,248,121 B1 | 6/2001 | Nobles | |
| 6,264,631 B1 | 7/2001 | Willis et al. | |
| 6,287,277 B1 | 9/2001 | Yan | |
| 6,447,472 B1 | 9/2002 | Moss | |
| 6,506,179 B1 | 1/2003 | Tiefenthal et al. | |
| 6,524,283 B1 | 2/2003 | Hopper et al. | |
| 6,740,273 B1 * | 5/2004 | Lee | 264/130 |
| 2001/0035590 A1 | 11/2001 | Nishi et al. | |
| 2002/0091365 A1 | 7/2002 | McNally et al. | |
| 2002/0198440 A1 | 12/2002 | Snow | |
| 2002/0198491 A1 | 12/2002 | Miller et al. | |
| 2003/0225369 A1 | 12/2003 | McMichael et al. | |

FOREIGN PATENT DOCUMENTS

| | | |
|---|---|---|
| CA | 1299954 | 5/1992 |
| CA | 2347208 | 4/2000 |
| DE | 9208103 U | 3/1993 |
| EP | 0347458 B1 | 3/1994 |
| EP | 0409436 B1 | 12/1994 |
| EP | 0943354 A1 | 9/1999 |
| GB | 2 218 372 A | 11/1989 |
| WO | WO 88/05316 | 7/1988 |
| WO | WO 00/23136 | 4/2000 |
| WO | WO 00/40289 | 7/2000 |
| WO | WO 02/22198 A2 | 3/2002 |
| WO | WO 02/051490 | 7/2002 |
| WO | WO 02/087492 | 11/2002 |
| WO | WO 03/032892 A2 | 4/2003 |

OTHER PUBLICATIONS

"PEG Percutaneous Endoscopic Gastrostomy", Brochure, one page, Create Medic Co., Ltd.

"Replacement Catheter", Japanese Brochure, one page.

Patent Abstracts of Japan, Publication No. 2000254221, Sep. 19, 2000.

* cited by examiner

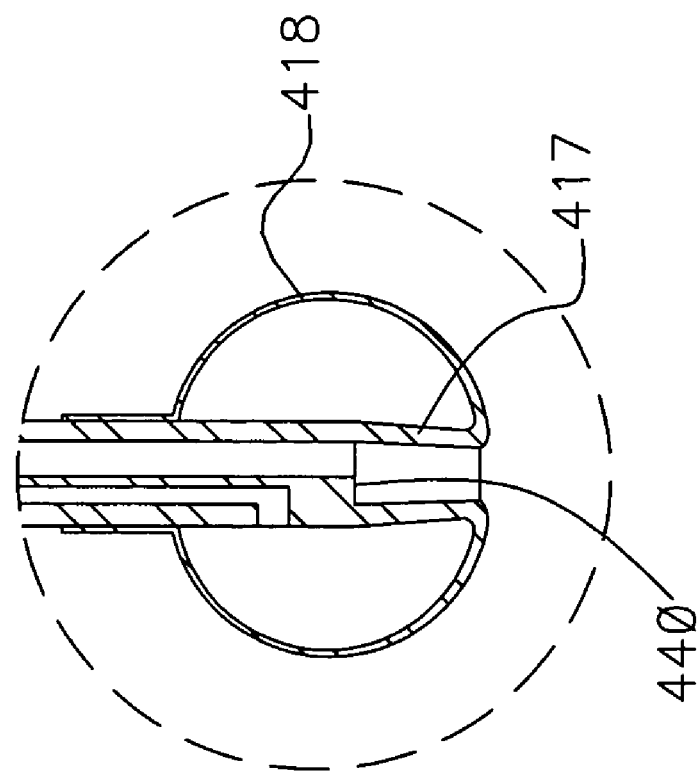
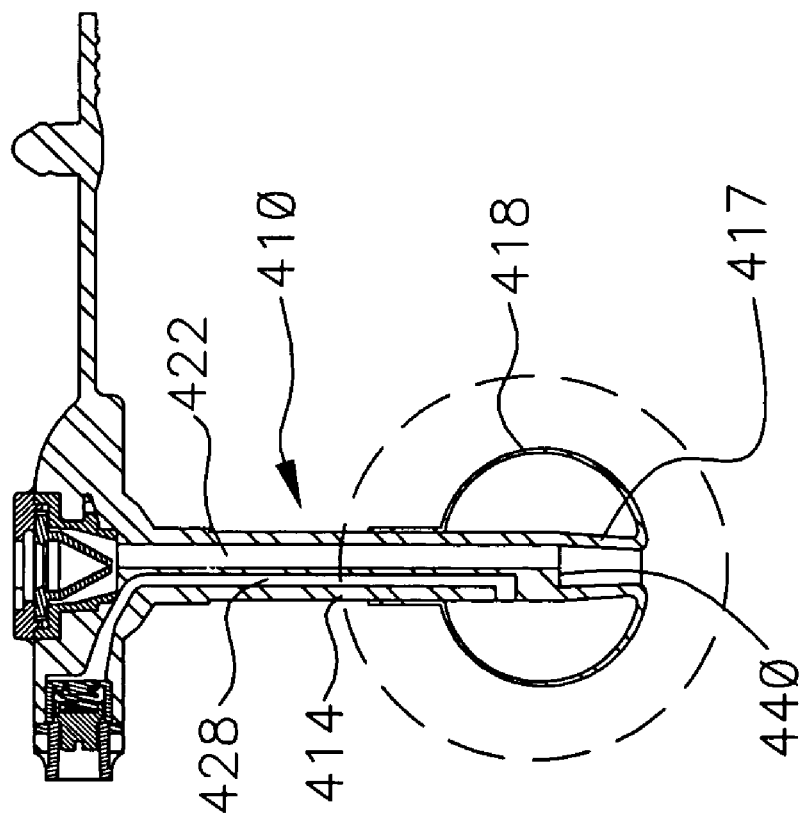

PROCESS FOR PRODUCING A CATHETER

BACKGROUND

Catheterization of a body cavity is frequently performed in medical procedures either to insert substances into or to remove substances from the body. During many of these procedures, it is necessary to keep the catheter in a relatively stable position to perform the desired insertion or removal. With the use of enteral feeding catheters (i.e., catheters which enable the administration of nutritional solutions directly into the stomach or intestines), for example, it is necessary to ensure that the catheter is not accidentally removed from the stomach or intestines. This is true both during the actual administration or removal of fluids, and the time periods in between.

In order to ensure that a catheter is maintained in the proper position, i.e. not accidentally removed or displaced, it is common to use a balloon disposed near the distal (patient) end of the catheter shaft. Inflating the balloon causes the balloon to contact the anatomical structure (i.e., a duct or stomach wall) and thereby prevents the catheter from moving out of the proper position. In the case of enteral feeding, a stoma is formed leading into the stomach or intestine. The catheter is positioned to extend through the stoma so as to form a channel into the stomach or intestines through which enteral feeding solutions may be instilled. Depending on the type of catheter, the balloon may be positioned in a variety of locations along the catheter shaft. For example, with a G-tube the balloon will generally be at or near the distal end of the catheter, although the balloon or other retention mechanism may be slightly closer to the head of the catheter provided that the retention effect may still be achieved.

FIG. 1 shows a side view of a prior art balloon catheter 10 (available from Ross Products Division of Abbott Laboratories, having offices in Abbott Park, Ill.) having a head 14 disposed at a proximal end 15 of the catheter 10. The head 14 contains valves (not shown) which regulate the flow of fluids through the balloon catheter 10. The head 14 also prevents the balloon catheter 10 from completely advancing through the stoma (not shown) and into the stomach or intestine of the user.

To prevent the catheter 10 from being pulled out of the stomach/intestinal wall, a balloon 18 is disposed along a catheter shaft 26. The catheter 10 is shown having an optional stiff tip 30, which is attached to the catheter shaft 26 at a distal end 17 opposite the head 14. The catheter shaft 26 is typically made of a medical grade silicone. The stiff tip 30, when present, is also frequently formed of a medical grade silicone but is usually configured to be as rigid as or less rigid than the catheter shaft 26.

The balloon 18 is advantageous because it allows the catheter shaft 26 to be inserted into the stoma (not shown) while the balloon 18 is uninflated. Once the catheter shaft 26 is properly positioned in the stoma, a syringe (not shown) is inserted into a side port 36 of the head 14 and a fluid is injected into the balloon 18 through a lumen (not shown in FIG. 1) of the catheter 10 so as to inflate the balloon 18.

While the balloon 18 remains inflated, the catheter 10 stays properly positioned in the stoma. The position of the balloon catheter 10 is maintained in such a manner until removal is desired. If the catheter 10 needs to be removed, the balloon 18 may be deflated so that it will not interfere with withdrawal of the catheter shaft 26.

The type of balloon 18 shown in FIG. 1 is fashioned around the perimeter of the catheter shaft 26 such that when it is deflated it reduces or contracts about the shaft 26. Although the balloon 18 will generally reduce or contract about the shaft 26, the balloon 18 clearly adds size to the portion of the catheter 10 which it surrounds.

Attachment of the balloon 18 to the catheter shaft 26 is frequently accomplished by gluing the balloon proximal end 20 and the balloon distal end 22 to corresponding positions on the external surface of the catheter shaft 26 so as to form a proximal cuff 32 and a distal cuff 34, respectively. Such cuffs 32 and 34 are longitudinal sections of the balloon 18 whose inside diameters correspond to the outside diameter of the shaft 26 at their respective points of attachment to the catheter 10 and have a distance between them which is about the length of the uninflated balloon 18. The cuffs 32 and 34 must be of sufficient length to provide a tight and durable seal between the balloon 18 and the catheter shaft 26.

While the prior art balloon configuration shown in FIG. 1 works to maintain the balloon catheter 10 in the proper position within the patient, balloon catheters of this type as well as the other known balloon catheters do have disadvantages. For example, one drawback of prior balloon catheters is discomfort to the user. With regard to the catheter of FIG. 1, in order to allow insertion of the catheter 10, the catheter shaft 26 and especially the stiff tip 30 must be relatively rigid or firm to prevent buckling under insertion pressures. However, this same firmness makes the distal tip 30 much more prone to irritate anatomical structures which come into contact with it. This is especially true in the stomach and intestines where the opposing walls of the anatomical structures tend to collapse on each other during physical exertion or when the cavity has little or no food. As the person moves, the stiff tip 30 repeatedly engages the adjacent anatomical structure (such as the stomach wall) and can lead to irritation and/or discomfort for the user. Thus, as the presence of an extended stiff catheter tip in this environment has been suspected of irritating the opposing surfaces of the body cavity, it would be desirable if the patient could be protected from exposure to the tip 30.

Accordingly, there is a need in the art for a balloon catheter with a distal tip which may be isolated from opposing internal body cavity surfaces.

Another disadvantage with the prior art balloons of the type discussed above, is that if they were to be secured to the interior portion of the tip 30 they would provide undesirable restriction of the flow of fluids therethrough. Although not done in prior catheters, if the tip were to be attached to the interior of the catheter shaft, the flow would be further reduced. The reduction in flow can result in the need for longer use of the catheter to obtain the desired level of fluid flow. If a catheter having a wider tip or shaft is used to overcome the fluid flow issue, the stoma through which the catheter must be inserted will need to be larger thereby creating other issues, such as increased time for the stoma to heal as well as creating a larger opening through which fluids can leak out.

Accordingly, there is a need for a catheter which can provide for an increased level of fluid flow (as compared with prior devices) without the need for a larger stoma opening.

Yet another disadvantage with prior art catheters of the type discussed above is that they generally first require the separate manufacture of multiple pieces (e.g., the catheter, the rigid tip and the balloon), then the attachment of the tip to the catheter and one end of the balloon and, finally, the attachment of the second end of the balloon to the catheter. Each of the attachments methods have been done manually in the past. Naturally, this manual operation is slow, costly and inefficient. Further with each additional step in a process there exists an opportunity for error and waste of product. To avoid the additional production and assembly steps, in many prior catheters the balloon is attached directly to the outside of the catheter without a tip; however, catheters of this sort do not enjoy the benefits the tips may have to offer.

Thus, while there is a need for catheters, because of the number of individual pieces or members which comprise a catheter and because those pieces are typically assembled by hand or at least in multiple assembly steps, there is a need in the art for a catheter which requires less assembly, and specifically less manual assembly.

SUMMARY OF THE INVENTION

The present invention relates generally to catheters, and more particularly to a process for producing a tip member and securing the tip member to a catheter during production of the tip member.

In response to the difficulties and problems discussed above, a process for producing a catheter having a tip member produced thereon has been developed. More specifically, one embodiment of the invention is directed to a process which includes providing a catheter with a head, a shaft, and a distal end, and producing a tip member such that the tip member is secured to the distal end of the catheter during production of the tip member. The process may further include providing a balloon having a proximal end and a distal end, and securing the distal end of the balloon to the tip member and the proximal end of the balloon to the shaft.

Another embodiment of the present invention relates to a method of producing a catheter having a balloon member having a proximal end and a distal end, wherein the distal end of the balloon member is attached to the distal end of the catheter during production of the balloon member. More specifically, the method includes providing a catheter with a proximal end, a shaft, an interior, an exterior, and a distal end, and producing a balloon member having a proximal end and a distal end, such that the distal end of the balloon member is attached to the distal end of the catheter during production of the balloon member.

These and other features and advantages will be seen from the following detailed description of the drawings and from the claims.

BRIEF DESCRIPTION OF THE DRAWINGS

The above and other objects, features and advantages of the invention will become apparent from a consideration of the subsequent detailed description presented in connection with the accompanying drawings in which:

FIG. 6 is a cross-sectional view of a catheter of the present invention. The catheter is shown having a tip member integrally formed with the shaft; and FIG. 6A is an enlargement of the encircled area of FIG. 6.

DETAILED DESCRIPTION OF THE PRESENT INVENTION

Figure 1:
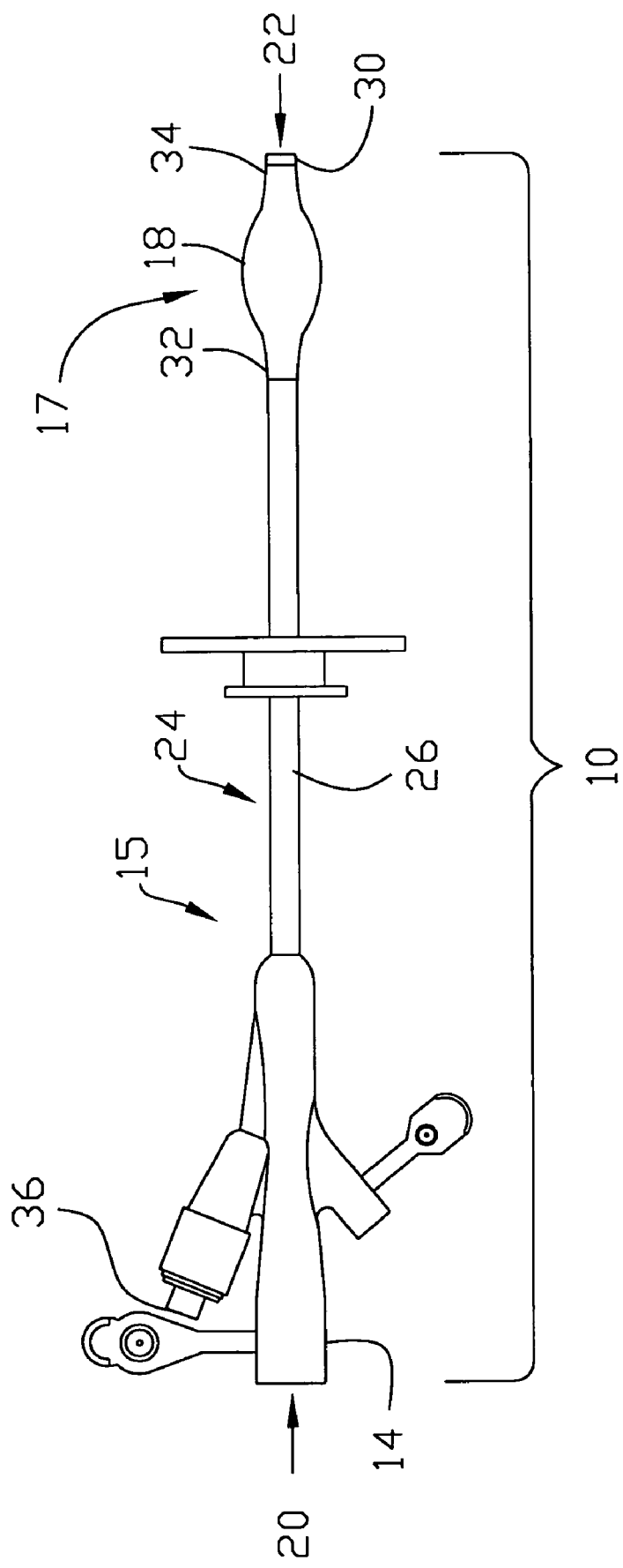
FIG. 1 is a side view of a prior art device.

As used herein, the term "distal" refers to the direction of the patient and the term "proximal" refers to the direction of the clinician.

One embodiment of the present invention relates to a process for producing a catheter including providing a catheter having a head, a shaft and a distal end, and producing a tip member such that the tip member is secured onto the distal end of the catheter during production of the tip member.

It will be appreciated that while reference is made to a tip member in the claims and in the first part of the disclosure, the term tip member is contemplated to mean or include, but is not limited to, tips of all shapes and sizes, a tip region, a tip portion, a unitary component, the portion of a unitary component containing a tip member, or the like. However, the term tip member will used throughout the remainder of the disclosure in place of the other terms for ease of reading and understanding the disclosure.

Another embodiment of the present invention is directed to process for making a catheter having a proximal end, a shaft, an interior, an exterior, a distal end and a balloon member which has a proximal end and a distal end. The process generally includes providing the catheter and producing the balloon member wherein the distal end of the balloon member is attached to the distal end of the catheter during the production of the balloon.

It will be appreciated that while reference is made to a means for expansion in the claims and in the first part of the disclosure, the term means for expansion may also mean or include, but is not limited to, a balloon, a sleeve, an elongate sleeve, an expandable sleeve, an expandable region or portion, an inflatable member, any other suitable expansion means or the like. However, for ease of reading and understanding of this disclosure and not intending to be limited thereby the term means for expansion will hereinafter be referred to as a balloon. It will also be appreciated that throughout the disclosure reference is made to inflation of the balloon, however, the present invention is not intended to be limited only to inflation. That is, while inflation is used herein for purposes of ease of reading and understanding the disclosure, the term inflation is also intended to mean or include, but is not limited to, expansion, enlargement, swelling or the like.

Reference will now be made to the drawings in which the various elements of the present invention will be given numeral designations and in which the invention will be discussed so as to enable one skilled in the art to make and use the invention. It should be appreciated that each example is provided by way of explaining the invention, and not as a limitation of the invention. For example, features illustrated or described with respect to one embodiment may be used with another embodiment to yield still a further embodiment. These and other modifications and variations are within the scope and spirit of the invention.

As used herein a singular term generally includes the plural, and a plural term generally includes the singular unless otherwise indicated.

Figure 2:
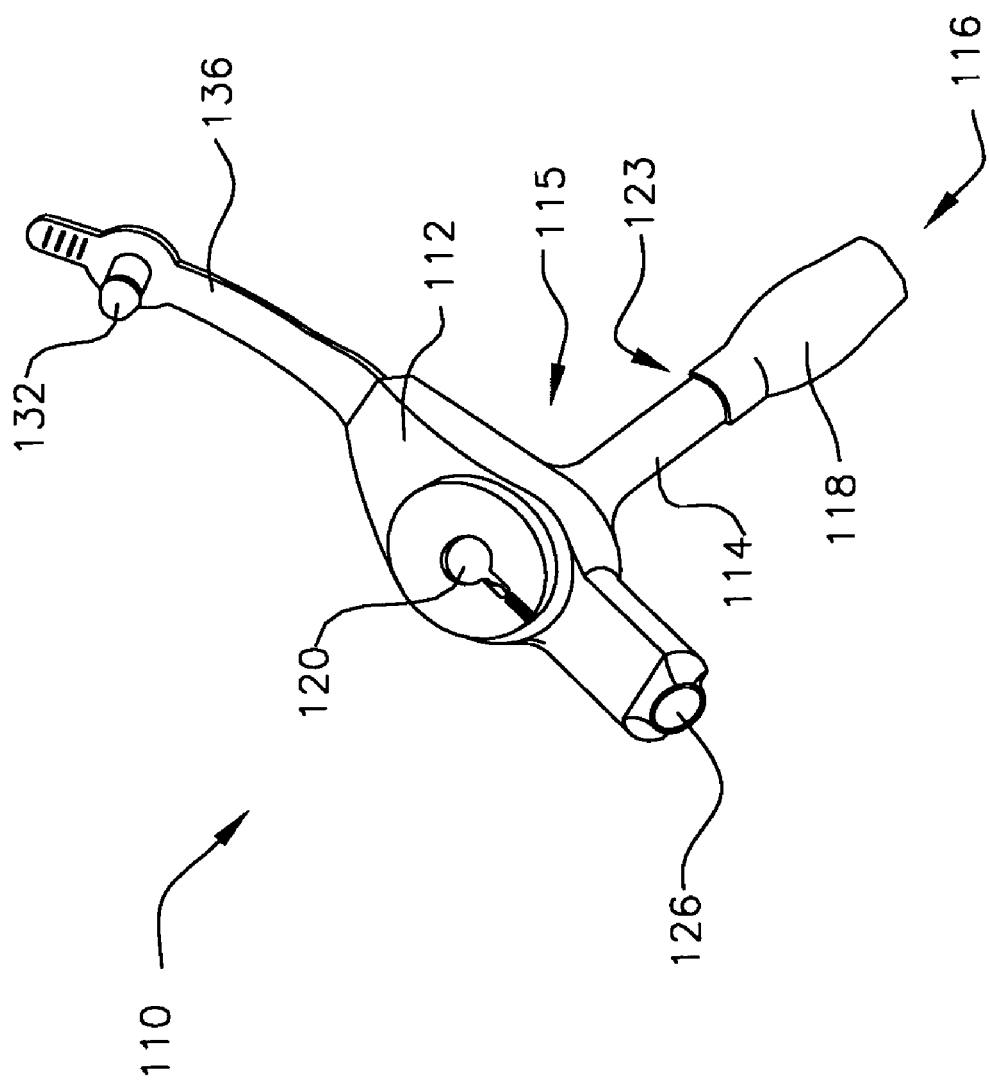
FIG. 2 is a perspective view of an embodiment of a catheter made in accordance with the present invention having a tip member at the distal end thereof.
Figure 3:
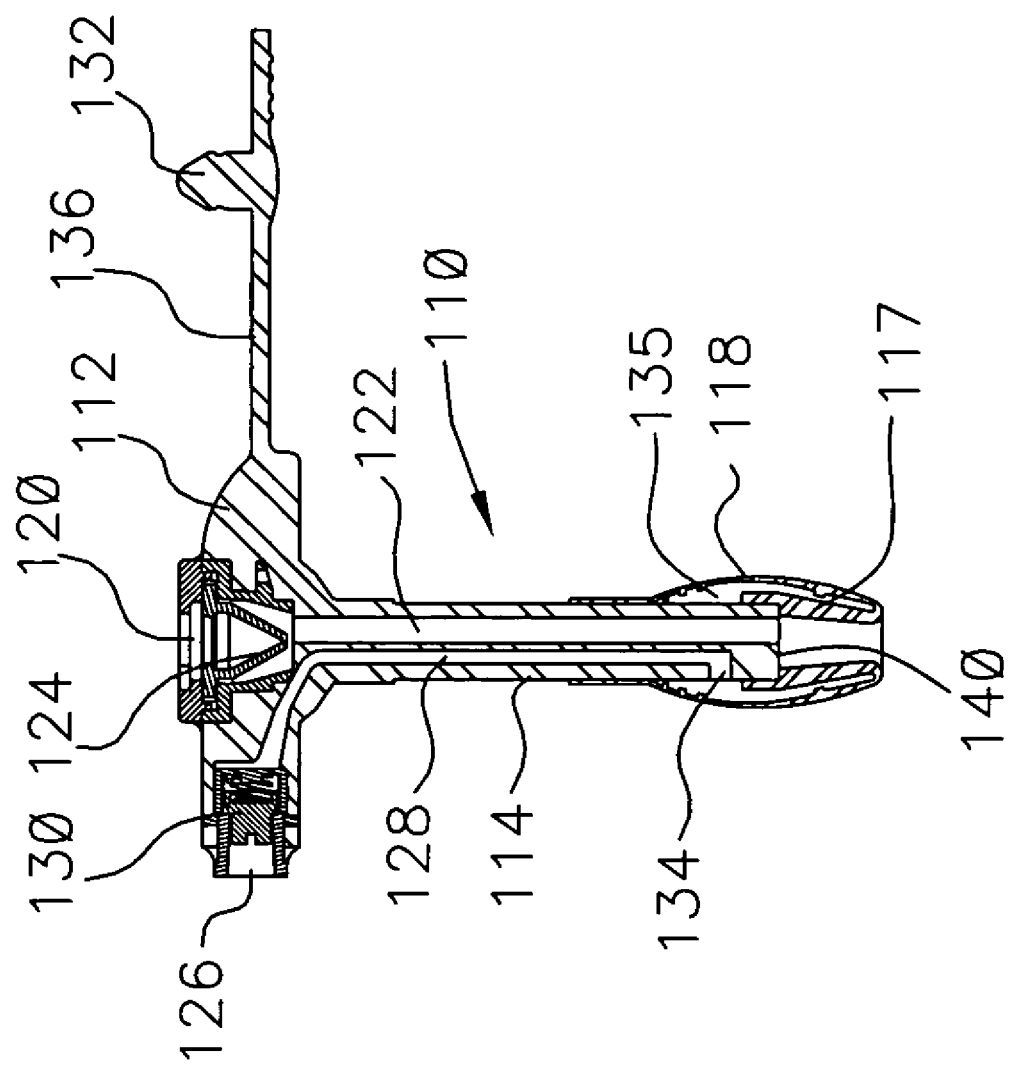
FIG. 3 is a cross-sectional view of the catheter of FIG. 2.

Referring now to FIGS. 2 and 3, there is shown a catheter 110 produced in accordance with a process of the present invention. The catheter 110 has a head 112, a shaft 114, a proximal end 115, and a distal end 116. FIG. 3 is the same catheter 110 as shown in FIG. 2, however, a cross-sectional view is provided to better enable discussion about the catheter 110 and the tip member 117 (FIG. 3). As shown in FIG. 3, the catheter 110 also includes a tip member 117 which is not part of the catheter 110 when the catheter 110 is originally formed; however, the tip member 117 is secured or otherwise attached to catheter 110 during the production of the tip member 117.

Although the tip member 117 is shown in FIG. 3 as a tapered member, as noted above, it will be appreciated that the term tip member may include any suitable tip member or attachment including, but not limited to, a tapered piece, a shaped piece, a unitary piece or component (such as that shown in FIGS. 3 and 6 and as discussed in commonly owned and co-pending U.S. patent application Ser. Nos. 10/306,999 and 10/306,994, entitled "CATHETER WITH UNITARY COMPONENT" and "PROCESS FOR PRODUCING UNITARY COMPONENT AND A CATHETER HAVING A UNITARY COMPONENT", respectively, both to McMichael et al., and both filed Nov. 30, 2002, each of which is incorporated by reference in its entirety herein), a means for expansion, or the like.

The various components of balloon catheter 110 may be made of any suitable material and may desirably be formed from bio-compatible materials such as medical grade silicone or the like.

The tip member 117 may be constructed in any number of suitable manners including, but not limited to, injection molding, transfer molding or dipping. As above, it is further contemplated that tip member 117 may be comprised of any material which makes it suitable for use in the present invention. Further, the material comprising tip member 117 may be the same or different and/or may have the same or different properties from that material which comprises the remainder of the catheter shaft 114 and balloon 118, if present.

Referring again to FIGS. 2 and 3, the catheter 110 is shown with a proximal opening 120 to a feeding lumen 122 (FIG. 3) within the shaft 114 for bolus feeding or providing other nutrient fluids, formula, and the like to a patient (not depicted). The lumen 122 (FIG. 3) may also be used to relieve or remove gases or other fluids. Although not required, an anti-reflux valve 124 (FIG. 3), which is generally included to prevent back-flow of the nutrient formula or the like, is shown disposed between the opening 120 and the lumen 122. Inflation port 126 is shown disposed in head 112 and communicates with inflation lumen 128 (FIG. 3) which extends longitudinally through the shaft 114.

As will be appreciated, the inflation port 126 and lumen 128 (FIG. 3) are optional in those embodiments not having or utilizing a balloon 118. That is, those embodiments which do not have a balloon or other means for expansion whose inflation or expansion is triggered by the application of internal fluid pressure or the exposure to another fluid or the like, need not include an inflation port 126 or lumen 128 as the means for expansion is either not present or does not require the inflation port 126 and/or lumen 128 to trigger its expansion.

However, in those embodiments having an inflation port 126 and lumen 128, such as the catheter 110 shown in FIG. 3, the inflation lumen 128 will generally terminate prior to reaching the distal end 116 of the catheter shaft 114. Thus, as shown in FIG. 3, the inflation lumen may terminate laterally to the shaft 114 at port 134 into the cavity 135 created by the balloon 118 and the shaft 114. A one-way valve 130 may be disposed between the inflation port 126 and the inflation lumen 128. Application of positive fluid pressure, such as with air or saline, within and/or upon the inflation lumen 128 by way of the inflation port 126 may cause the balloon 118 to inflate as shown in the alternate embodiments of FIGS. 4–6. Valve 130 (FIG. 3) helps prevent inadvertent deflation of the balloon 118 (FIG. 3). Also shown associated with the head 112 is a plug 132 (FIG. 3) for the proximal opening 120 (FIG. 3) and a lanyard 136 for retaining the plug 132 in a ready position. The plug 132 can be inserted in the opening 120 thereby reducing or precluding contamination when the opening 120 is not in use. Feeding lumen 122 (FIG. 3) extends longitudinally through shaft 114 and is shown terminating at the distal end 140 (FIG. 3) of the shaft 114.

It will be appreciated that the size of the catheter 110 as well as the length (inflated and uninflated) of the balloon 118 may be varied in accordance with the size and shape of the body cavity (not shown) the catheter 110 is to be used in and the nature of the matter to be moved through the catheter 110. That is, in some instances, it may be desirable to use catheters having larger and/or wider shafts than in other embodiments. Additionally, as discussed in more detail below the balloon 118 of the catheter 110 may be designed to have a certain size and/or shape in either or both of its inflated or uninflated configurations.

Although a stiff and/or tapered tip member 117 may provide benefits or advantages over catheters without such characteristics, many prior catheters were made without a tip because of the additional production and assembly steps that were required. Even when tips were included in prior catheters, for ease of manufacturing concerns, the prior catheters and the tips were made separately and later assembled. For example, one reason the tips were produced separately from the catheter and then later assembled therewith was that in many instances it was desirable for the tip 30 (FIG. 1) to exhibit different physical properties from the remainder of the catheter 10 (FIG. 1) whether the material used to construct the tip 30 and the catheter 10 was the same or not. As noted above, once the separate components were produced, they had to be assembled, and, whether mechanically or manually assembled, because the assembly was done separate from the production of the components the assembly required some kind of adhering or bonding agent (e.g., adhesives, glues, chemical bonding agents, etc.) to achieve the necessary attachment. The elimination of this separate attachment step and the reduced need for an adhering or bonding agent may result in productivity increases and efficiency as well as other cost savings.

To reduce the difficulties and problems associated with the separate production of the tips 30 (FIG. 1) and catheters 10 (FIG. 1), one embodiment of the present invention is directed to forming or producing a tip member 117 (FIG. 2) in such a manner that the tip member 117 is secured to or about (hereinafter secured to) the distal end 140 of a catheter 110 during production of the tip member 117. That is, for example, if the tip member 117 is to be produced by injection molding, the process may further include, but is not limited to, the positioning of the catheter 110, and specifically the distal end 140 thereof, sufficiently within a machine or device (not shown) in which the injection molding is occurring or is to occur so as to allow the tip member 117 to be produced and secured to the distal end 140 of the catheter 110 without interfering with the manufacture or production of the tip member 117. It will be appreciated that the term "secured" has been used in conjunction with production of the tip member 117 and its final placement with respect to the catheter 110, however, this term is used for ease of description and reference herein and is not intended to be limited in any manner. For example, the term "secured" may also mean or include, but is not limited to, formed with, attached, fixed to, affixed, joined, fastened or the like.

In some production steps it may be necessary to use a mandrel, core pin (not shown) or the like to create or maintain the interior passageways (e.g. lumens) in the shaft 114 or the tip member 117. As shown in FIG. 3, tip member 117 may, for example, be attached to the catheter 110 in such a way as to overlap with the distal end 140 of the catheter 110. This overlap may be on the outside such that the tip member 117 is secured to the outside or exterior of the catheter 110 (FIGS. 3–5), or the overlap may be on the inside or interior (not shown) of the catheter 110. Where the attachment is to the interior of the catheter shaft 114, the attachment is desirably such that the tip member 117 does not block or significantly reduce the flowthrough capabilities of the catheter.

Alternately, for example, as shown in FIGS. 6 and 6A and as shown and discussed in co-pending applications "CATHETER WITH UNITARY COMPONENT" and "PROCESS FOR PRODUCING UNITARY COMPONENT AND A CATHETER HAVING A UNITARY COMPONENT", incorporated by reference above, the tip member may be an unitary component secured to the end of the catheter shaft in such a way that there is little or no overlap and such that little or no restriction of the passageway or lumen occurs as a result of the securement of the tip member. Note that some restriction may occur where the tip member is tapered or otherwise shaped; however, such restriction is different than any restriction resulting from the manner in which the tip member is secured.

Another embodiment of the present invention relates to a process for producing a catheter 210 (FIG. 5) having a balloon member 218 attached to the distal end 240 of the catheter 210 during production of the balloon member 218. The process generally includes providing a catheter 210 with, a shaft 214, a proximal end 215, an interior, an exterior, and a distal end 240, and producing a balloon member 218 having a distal end 221 and a proximal end 223. It will be appreciated that the balloon member 218 may consist of any suitable material or product including, but not be limited to, elastomeric or expandable materials. As suggested above, the distal end 221 of the balloon member 218 is shown in FIG. 5 as being attached to the distal end 240 of the catheter 210 during production of the balloon member 218.

Figure 5:
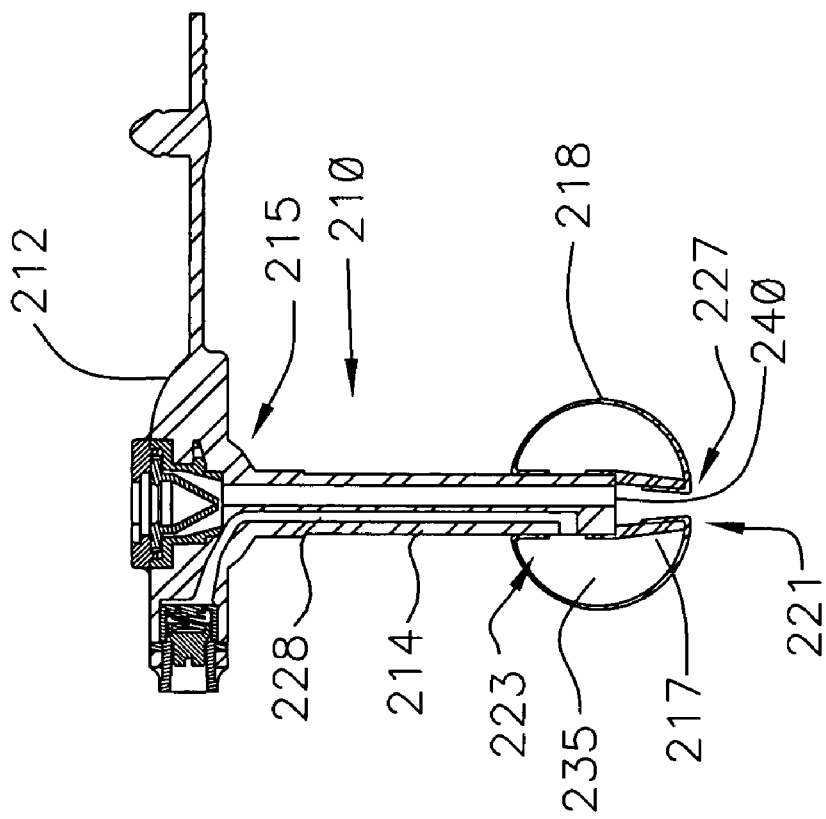
FIG. 5 is a cross-sectional view of an embodiment of the present invention having an inflated balloon member attached to a tip member.

It will be appreciated that the proximal end 223 (FIG. 5) of a balloon member 218 may also be attached to the catheter 210 (FIG. 5). In many, but not all, instances the balloon member proximal end 223 (FIG. 5) will need to be attached to catheter 210 (FIG. 5) to form an expandable cavity 235 between the balloon member 218 and the catheter 210. In those instances in which the proximal end 223 of the balloon member 218 is secured to the catheter 210, it may be done in any suitable manner which may include, but is not limited to, gluing, chemical bonding, or the like. The balloon member 218 may be formed such that at least one end thereof may be attached to the interior of the catheter 210 (e.g. shaft 226 or tip member 217). Alternatively, the balloon member 218 may be formed such that at least one end thereof may be attached to the exterior of the catheter 210. Still another embodiment of the present invention may include an inverted attachment or cuff 223 as shown in FIGS. 5. More specifically, for example, the proximal end 223 of the balloon member 218 may be attached to the shaft 214 of the catheter 210 in an inverted manner. The advantages and benefits of such an inverted attachment are discussed in commonly owned and co-pending U.S. patent application Ser. No. 10/307,057, entitled "CATHETER HAVING A BALLOON MEMBER INVERTEDLY ATTACHED THERETO", filed on Nov. 30, 2002 in the names of Letson et al., the disclosure of which is incorporated by reference in its entirety herein.

Referring to FIG. 6, it will be appreciated that the distal end 440 of the catheter 410 may further include a tip member 417. The tip member 417 may be integrally formed with (i.e., part of) the catheter 410 or the tip member 417 may be separately produced and attached at a some point after initial production of the catheter (as shown in FIG. 5). In either case, for purposes of discussion in connection with this aspect of the present invention, where a tip member 417 (FIG. 6) is already present (whether integrally formed or separately produced and later attached, including by the processes described above) the distal end 227 (FIG. 5) or 427 (FIG. 6) of the tip member 217 (FIG. 5) or 417 (FIG. 6) may be considered to be the distal end of the catheter.

Figure 4:
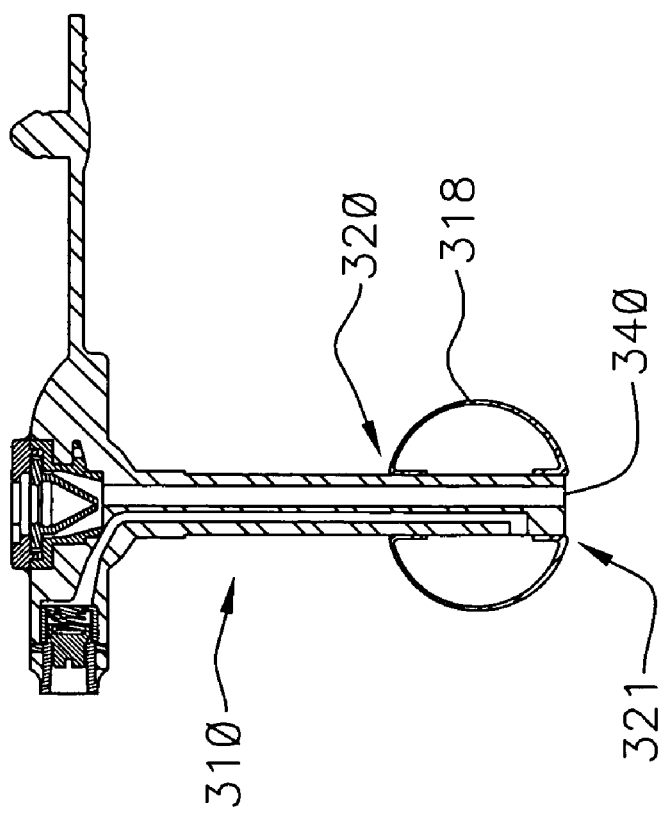
FIG. 4 is a cross-sectional view of an embodiment of the present invention having an inflated balloon member attached to the distal end of the catheter.

It is contemplated that a catheter 310 such as the one shown in FIG. 4 will include a balloon member 318 and that the balloon member 318 shall attach to the distal end 340 of the catheter 310 or any intervening product or component which still provides or allows for the function of the present invention. That said, the balloon member 318 of the present embodiment should be attached to the distal end 340 of the catheter 310 during production of the balloon member 318. More specifically, the distal end 321 of the balloon member 318 may, for example, be secured to the interior or to the exterior of the distal end 340 of the catheter 310 during the production of the balloon member 318.

The step of producing the balloon member 318 (FIG. 4) in this embodiment may be performed in any suitable manner. Exemplary suitable ways of producing the balloon member 318 include, but are not limited to, injection molding, transfer molding, dip molding and the like. It will be appreciated, as indicated above, that the production of the balloon member 318 may require the use of a mandrel, core pin (not shown) or the like which may be used to assist in the formation of the balloon member 318 and/or to create or maintain one or more passageway (e.g. lumen) through the catheter 310, distal end 340 and/or tip member (not shown in FIG. 4). If mandrel or core pin is used, it will be removed from the balloon member 318 after the balloon member 318 has been produced or substantially produced.

The exact manner in which the balloon member 318 is attached to the catheter 310 or end 340 is not critical, rather only that the balloon member 318 be attached during its production. It will be appreciated that a balloon member 318, as with most other objects, does not have an exact point of formation or production. That is, an exact point of formation or production is not typically readily identifiable visually. More specifically, for example, when an object or item is being made it usually takes several steps to do so and/or something typically transforms into an object gradually rather than instantaneously. Thus, generally after something is made time must pass before the object is complete. That is, for example, to make something via injection molding, one generally begins by mixing the ingredients or compounds, and then injecting the mixture into a mold under certain temperature and/or pressure conditions. The mixture in the mold is typically cooled or allowed to return to ambient conditions. At some point after the mixture is injected into the mold, the mixture is considered to have been molded and is removed from the mold, even though the mixture may continue to cool or otherwise attempt to reach equilibrium with the environment after being removed from the mold. Accordingly, while the item has been molded, the production of that item does not end until the item has cooled and/or reached an equilibrium with the environment. Thus, for purposes of this description, the production process will not be deemed to be complete until the object has substantially reached equilibrium with an environment the object is likely to be used or stored in. Accordingly, for example, if a object is produced according to one method of injection molding, the production is not complete until the product sets and/or cools or otherwise reaches or substantially reaches equilibrium with an environment the object is likely to be used or stored in.

It is of note that the use of an environment with elevated temperatures or conditions (as compared to the environment in which the object may be used or stored) which allows the object's production to be temporarily suspended is contemplated as just that, a suspension and that even though the object may have completely formed (e.g. taken shape), production of the object is not complete until it is allowed to reach the above described condition(s) with an environment in which it is likely to be used or stored. It will be recognized that this principle or concept may apply to other suitable production processes and embodiments. Thus, for example, if a dipping process is used to produce a tip member or a balloon member in accordance with the present invention, the production of the tip member or balloon member can, but need not, be done by inserting the distal end of a catheter into the dipping solution, as the production of the balloon member or tip member should not be considered complete until the resulting member is cooled and/or substantially set. As such, the present invention contemplates and is intended to include, for example, either the formation of a balloon member or tip member via dip molding on a core pin and the later attachment of the balloon member or tip member to a catheter before the production of the resulting balloon member or tip member is complete, or the formation of the balloon member or tip member directly onto the catheter shaft.

While the invention has been described in detail with respect to specific embodiments thereof, those skilled in the art, upon obtaining an understanding of the invention, may readily conceive of alterations to, variations of, and equivalents to the described embodiments and the processes for making them. It is intended that the present invention include such modifications and variations as come within the scope of the appended claims and their equivalents.

What is claimed is:

1. A process for producing a catheter comprising:
providing a catheter shaft having a proximal end, a distal end, an interior, an exterior, a first lumen extending through the shaft and exiting at the distal end, and a second lumen extending at least partially through the shaft and terminating in a port situated upon the exterior;
situating the distal end of the shaft within a molding device;
forming in place on the distal end of the shaft within the molding device a unitary component having a first surface, a rigid tip interconnected to an expandable balloon, the unitary component terminating in a distal end at the tip and a proximal end at the balloon, the unitary component having a passageway therethrough and being securely affixed to the distal end of the shaft by being formed in place such that the first lumen and passageway are in alignment with one another;
folding the proximal end of the unitary component over the rigid tip; and
attaching the proximal end of the unitary component to the exterior such that the first surface of the tip faces the first surface of the expandable balloon and the port is contained within a space formed by the expandable balloon.

2. The process of claim 1 wherein the unitary component is secured to the interior of the catheter.

3. The process of claim 1 wherein the unitary component is secured to the exterior of the catheter.

4. The process of claim 1 wherein the unitary component is secured to the catheter so as not to substantially overlap the distal end of the catheter.

5. The process of claim 1 wherein the proximal end of the expandable balloon is attached to the catheter in an inverted manner.

6. The process of claim 1 comprising a seamless intersection between the tip and expandable balloon of the unitary component.

* * * * *